(12) United States Patent
Bermudez Rodriguez et al.

(10) Patent No.: US 11,246,269 B2
(45) Date of Patent: Feb. 15, 2022

(54) AUTONOMOUS MOBILE PLATFORM AND VARIABLE RATE IRRIGATION METHOD FOR PREVENTING FROST DAMAGE

(71) Applicant: INTERNATIONAL BUSINESS MACHINES CORPORATION, Armonk, NY (US)

(72) Inventors: Sergio A. Bermudez Rodriguez, Boston, MA (US); Levente Klein, Tuckahoe, NY (US); Alejandro G. Schrott, New York, NY (US); Theodore G. van Kessel, Millbrook, NY (US)

(73) Assignee: INTERNATIONAL BUSINESS MACHINES CORPORTATION, Armonk, NY (US)

( * ) Notice: Subject to any disclaimer, the term of this patent is extended or adjusted under 35 U.S.C. 154(b) by 138 days.

(21) Appl. No.: 16/241,479

(22) Filed: Jan. 7, 2019

(65) Prior Publication Data
US 2019/0141912 A1 May 16, 2019

Related U.S. Application Data

(63) Continuation of application No. 14/976,336, filed on Dec. 21, 2015, now Pat. No. 10,219,448.

(51) Int. Cl.
*A01G 13/06* (2006.01)
*G01N 33/24* (2006.01)
(Continued)

(52) U.S. Cl.
CPC ............ *A01G 13/065* (2013.01); *A01B 79/00* (2013.01); *A01G 25/167* (2013.01);
(Continued)

(58) Field of Classification Search
CPC ...... A01G 25/167; A01G 25/09; A01G 13/06; A01G 13/065; A01G 25/16
(Continued)

(56) References Cited

U.S. PATENT DOCUMENTS 4,015,366 A * 4/1977 Hall, III ............... A01D 46/005
47/1.43
4,039,144 A * 8/1977 Mee ..................... A01G 13/065
239/2.1
(Continued)

FOREIGN PATENT DOCUMENTS

| WO | 00/42843 | 7/2000 |
| WO | 2005/026442 A1 | 3/2005 |
| WO | 2014/108891 A1 | 7/2014 |

OTHER PUBLICATIONS

Feddersen, English translation of DE3614179, Oct. 1987, classified in A01G25/09. (Year: 1987).*

(Continued)

*Primary Examiner* — Chee-Chong Lee
(74) *Attorney, Agent, or Firm* — Tutunjian & Bitetto, P.C.; Stosch Sabo

(57) ABSTRACT

A rover includes a base having wheels and a propulsion system coupled to the wheels to propel the rover around a field. A tower is coupled to the base and extends over the base. Sensors are set on the tower and the base and are configured to sense environmental conditions around the rover at different elevations. A computing system includes a processor and memory. The memory is configured to receive measured data from the sensors and determine an amount and manner of water to be dispensed on plant life in the field.

9 Claims, 3 Drawing Sheets

(51) Int. Cl.
*G05D 1/00* (2006.01)
*G05D 1/02* (2020.01)
*A01G 25/16* (2006.01)
*A01B 79/00* (2006.01)
*A01G 25/09* (2006.01)

(52) U.S. Cl.
CPC ......... *G01N 33/246* (2013.01); *G05D 1/0088* (2013.01); *G05D 1/0278* (2013.01); *A01G 25/09* (2013.01)

(58) Field of Classification Search
USPC .......................................................... 239/11
See application file for complete search history.

(56) References Cited

U.S. PATENT DOCUMENTS

| | | |
|---|---|---|
| 4,532,757 A | 8/1985 | Tutle |
| 4,843,561 A | 6/1989 | Larson |
| 5,523,761 A | 6/1996 | Gildea |
| 5,557,656 A | 9/1996 | Ray et al. |
| 6,320,898 B1 | 11/2001 | Newson et al. |
| 6,516,271 B2 | 2/2003 | Upadhyaya et al. |
| 6,549,835 B2 | 4/2003 | Deguchi et al. |
| 2005/0067511 A1 | 3/2005 | Gray et al. |
| 2007/0010915 A1* | 1/2007 | Burson ................. A01G 25/16 700/284 |
| 2009/0077877 A1 | 3/2009 | Kerber et al. |
| 2010/0179734 A1* | 7/2010 | Schumann .......... A01M 7/0089 701/50 |
| 2011/0079654 A1 | 4/2011 | Bailey et al. |
| 2011/0247264 A1 | 10/2011 | Luciano, Jr. et al. |

OTHER PUBLICATIONS

List of IBM Patents or Patent Applications Treated as Related dated Jan. 7, 2019, 2 pages.
Loseke, B. et al., "Preventing spring freeze injury on grapevines using multiple applications of Amigo Oil and naphthaleneacetic acid" Scientia Horticulturae (2015) pp. 294-300, vol. 193.
Trought, M.C.T et al., "Practical Considerations for Reducing Frost Damage in Vineyards" Frost Damage and Management in New Zealand Vineyards (1999) pp. 1-43.
U.S. Office Action issued in U.S. Appl. No. 15/350,437 dated Dec. 28, 2017, pp. 1-18.
U.S. Office Action issued in U.S. Appl. No. 15/350,465 dated Dec. 29, 2017, pp. 1-18.

* cited by examiner

AUTONOMOUS MOBILE PLATFORM AND VARIABLE RATE IRRIGATION METHOD FOR PREVENTING FROST DAMAGE

BACKGROUND

Technical Field

The present invention relates to mobile platforms for agriculture, and more particularly to systems and methods for detecting onset of frost damage and ways to prevent it by minimizing inputs to save plant life.

Description of the Related Art

Damage to crops by freezing temperatures can cause large amounts of crop losses every year. A number of different methods are available for preventing frost damage to crops. The methods are described in terms of active and passive techniques. Active methods are those which are used when the danger of a freeze is present and include such techniques as adding heat and covering crops. Passive methods are those which are used well in advance of the freeze and include proper scheduling of planting and harvesting within a safe freeze-free period, proper crop and field selection, etc. The terms frost and freeze are often used interchangeably for the subfreezing temperature conditions that cause crop damage. In general, any prevention method may use a uniform approach where the whole farm or crop planted in a certain area is treated in the same way.

SUMMARY

A rover includes a base having wheels and a propulsion system coupled to the wheels to propel the rover around a field. A tower is coupled to the base and extends over the base. Sensors are set on the tower and the base and are configured to sense environmental conditions around the rover at different elevations. A computing system includes a processor and memory. The memory is configured to receive measured data from the sensors and determine an amount and manner of water to be dispensed on plant life in the field.

A rover system includes a self-propelled rover including a tower coupled to a base and extending over the base and a plurality of sensors set on the tower and the base and configured to sense environmental conditions around the rover at different elevations. A computing system includes a processor and memory. The memory is configured to receive measured data from the plurality of sensors and determine an amount and manner of water to be dispensed on plant life in the field. A sprinkler system includes a plurality of individually controllable heads. The heads are responsive to measured data from the plurality of sensors to apply water to the plant life in accordance with local conditions.

A method for dispensing water for crops includes traversing a field with a self-propelled rover, the rover including a tower coupled to a base and extending over the base and a plurality of sensors set on the tower and the base, the tower and base configured to sense environmental conditions around the rover at different elevations and at different locations in the field; measuring the environmental conditions using the plurality of sensors on the rover at the different elevations and at the different locations in the field; evaluating local measurement data to determine an amount and manner for disbursement of water under the environmental conditions for the different elevations and at the different locations in the field; and delivering the water until goal conditions are met.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Figure 1:
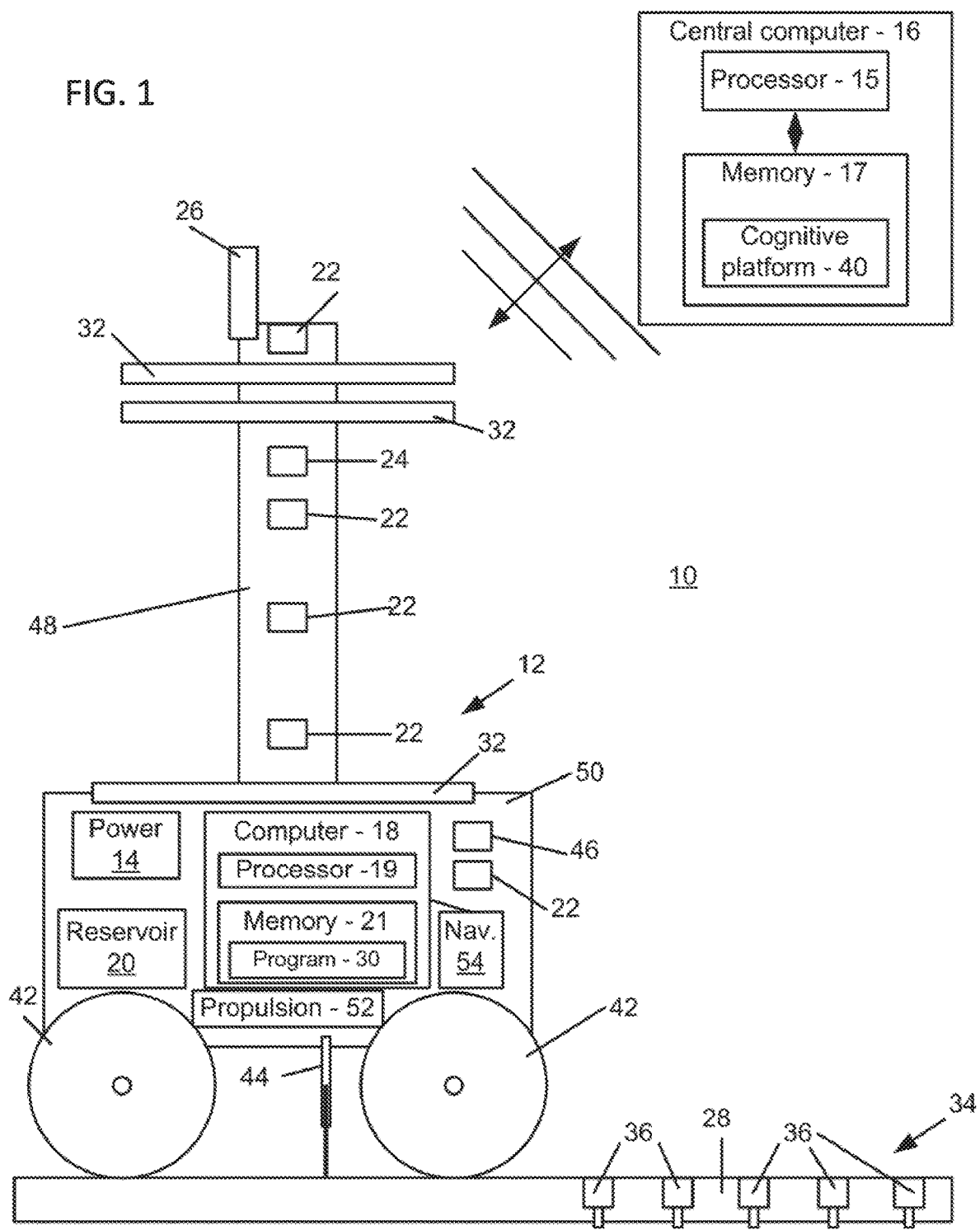
FIG. 1 is a schematic diagram showing a rover system in accordance with the present principles.

In accordance with the present principles, systems and methods are provided to prevent frost damage to crops or other plants in an outdoor environment. The present principles are especially applicable to vineyards, berry farms, citrus farms and other commercial crops. Vineyards will be employed herein as an example. In one embodiment, a system dispenses water uniformly in accordance with conditions measured using environmental variables from a weather station and, in particular, related to air inversion phenomena, which can result in very low temperatures in vineyards in early spring. These conditions may be measured regionally and assume that data will be very similar across the whole region, e.g., over multiple farms, or derived by monitoring/forecasting weather; however, crop freeze may be dependent on very local conditions.

The systems and methods address frost potential in different ways. For example, the land can be irrigated a day ahead of a frost to trap heat in the soil that would be released during the frost period. Since local conditions may be estimated based on existing data, to account for inaccuracy of the data, over watering may be preferred to prevent damage. A local micro sprinkler system may be employed to disperse water on grapes, and a continuous water stream will prevent frost damage by providing continuous water to leaves/buds and maintaining the temperature of ice at about 27° F. The micro sprinkler system may include nozzles that act to provide water dispersion above the grapes to form snow to cover the grapes.

In one embodiment, a mobile sensing platform is employed that moves through a vineyard and measures the local temperature changes at different heights. An onboard processor can compute temperature profiles and estimate the likelihood for air inversion. The rate of cooling of the temperature is recorded in different locations that may indicate the speed by which the inversion may occur.

The platform can send a command to a central computer that can control and adjust the amount of water dispersed by a micro sprinkler system. Sprinkler heads of the micro sprinkler system can be addressed individually or in a group, and can be controlled to overcome the local adverse conditions in the weather. The platform may be equipped with cameras to obtain a visualization to generate a feed-back loop for optimization of the process. The system may include data acquisition and transmission of the data and a controlled variable rate sprinkler system to enable water spraying to prevent frost damage in a vineyard or orchard setting.

The sprinkler system may be employed to disperse water when the temperature is below the freezing point. When water freezes on the leaves of plants, heat is also released to the atmosphere. The sprinkler system provides water to be dispersed on ice to create a protective ice coating and maintain the temperature at a water-ice equilibrium point. The present sprinkler system can dispense water differentially based on the measurement of a rover and accounts for spatial variability instead of being based on a single weather data station measurement that forces uniform water dispensing.

The use of sprinklers can protect vines when temperatures fall to, e.g., −3.9° C. (25° F.), under certain conditions. Water from the sprinklers supplies heat to the vine-water-atmosphere system, and the heat is released as water cools to 0° C. (32° F.) and then freezes to ice. One factor to be considered in this situation is the heat of fusion (released as water freezes to ice). A gallon of water releases 300 kcal (1200 BTU) of heat as it freezes. Water also evaporates in the vine-water-atmosphere system. The evaporation of water causes a loss of 2300 kcal (9000 BTU) per gallon. Therefore, to maintain a positive heat balance, more water needs to freeze than to evaporate. This amount has been determined to be a factor of 7.5 units of water or more for every unit of water that evaporates. This, along with a buffer for the humidity of the air and wind speed (factors which can increase the evaporation rate) is a basis for the sprinkler application rate employed. An application rate may be between about 6.9 to about 8.2 hectare-millimeters (0.11 to 0.13 acre-inches) per hour or a pumping capacity of 470 liters per minute per hectare (50 gallons per minute per acre). Furthermore, use of snow generated by a distinct actuation of the sprinkler system may be more employed in certain air temperature stratification conditions.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a rover system 10 is depicted in accordance with one illustrative embodiment. The rover system 10 includes a rover 12. The rover 12 may include a vehicle configured to traverse a field to measure the local environmental conditions. The rover 12 may be equipped to transmit a command to a central computer 16 and also has the ability to dispense water to prevent frost damage or irrigate plants.

In one embodiment, the rover 12 includes a base 50 having wheels 42. The wheels 42 are configured for the terrain of a vineyard or other field. The rover 12 may include two wheels (with gyroscopic stabilization), three wheels, four wheels, etc. A propulsion system 52 is coupled to the wheels 42 to propel the rover around a field 28. The propulsion system 52 may include a battery driven engine, an internal combustion engine, a solar powered engine, a wind powered engine or any other power source/engine. The rover 12 may be equipped with a localization system or navigation system 54, e.g., a global positioning system (GPS), or can be equipped with a kinematic GPS connected either to a satellite or to a local receiver/transmission point that can be localized within, e.g., 1 foot distance. The navigation system 54 may be loaded on an onboard computer system 18 or may be a separate device or devices.

The navigation system 54 permits a sensing system to be realized, e.g., in a cognitive computing platform 40, to know a position in a field at which measurements and water dispensing occurs. The navigation system 54 may include at least one of: a GPS sensing system, a dead reckoning system using encoders in the wheels 42 to track position from a known starting point and a radio direction sensing system that permits navigation relative to one or more fixed transmitters (e.g., in a central computer 16 or located at fixed positions in the field).

The cognitive platform 40 includes a program by which the user can direct the rover 12 to follow a desired route and time interval of travel through the field. This may include at least one of: manually guiding the rover 12 through the field and recording the path for future use, a list of sequential GPS or radio location points to follow and a desired time interval between location points and a desired speed of travel. The cognitive computing platform 40 further employs the navigation system 54 to estimate the condition of the field in three spatial dimensions based on the travel history of the rover 12 and an altitude of sensor measurements, as will be described.

The program of the cognitive computing platform 40 further estimates the time variation of the above multidimensional measurements (temperature, humidity, dew point, wind speed, etc.) and provides estimates of future field conditions, and further utilizes the physical measurements to estimate state variables of the field including but not limited to plant saturation, energy content, water loss rate, etc. These and other factors may be applied to water dispensing computations calculated by the cognitive platform 40 (in computer system 16 or 18).

The rover 12 includes a power source 14 that may include a battery, solar cell, wind turbine, internal combustion engine, electric engine, etc. A tower 48 is coupled to the base 50 and extends over the base 50 in operational scenarios. The tower 48 may be retractable (extendable) for easy storage or to protect the rover 12 under inclement weather conditions. The height of the tower 48 may be adjusted to permit measurements at different heights for a given set of conditions. The height of the tower 48 can be as high (or higher) the trees/plants being protected or cared for. A plurality of sensors 22 is set on the tower 48 and/or the base 50 and are configured to sense environmental conditions around the rover 12 at different elevations. The rover 12 may be manually controlled and may be part of a known vehicle, such as a truck, tractor, pull cart, etc. The rover 12 may be self-propelled and may be remotely controlled or self-controlled.

In one embodiment, the central computer 16 controls the rover 12 and its operations. The central computer 16 includes a processor 15 and memory 17. The memory 17 is configured to receive measured data from the plurality of sensors 22 and an imaging device 24 and determine an amount and manner of water to be dispensed on plant life in the field. The rover 12 records local information with a very high spatial granularity and provides feedback to the system (16 and/or 18) to take action on the recorded local information.

In another embodiment, the rover 12 may include the onboard computer system 18 to control the movement and operations of the rover 12. The computer system 18 includes a processor 19 and memory 21. The computers 16 and 18 may share or distribute functions between them. In some embodiments, only the computer 18 is employed and in other embodiments only the computer 16 is employed. The functions and capabilities of the computers may be interchangeable. The computers 16 and 18 may include peripherals, displays, interfaces (mouse, keyboard, etc.), etc. to enable human interactions with the systems.

The rover 12 may include a reservoir 20 for carrying water and/or a solution that may prevent water freezing. Alternately, the reservoir 20 may be replaced by a supply hose that provides water to the reservoir/rover as needed. In other embodiments, water is supplied by a sprinkler system 34, which can be an in-ground sprinkler or drip system or be an above-ground sprinkler or drip system. The sprinkler system 34 is controlled based on the rover 12 or feedback from the rover 12.

The rover 12 preferably includes an autonomous mobile platform, but may include a vehicle mountable platform that can be conveyed on a, e.g., a truck driven by a farmer, etc. The rover 12 is equipped with environmental sensors 22 and the imaging device 24. The sensors 22 may include a plurality of different sensor types to measure, for example, temperature, relative humidity, dew point, wind velocity at different heights above a ground 28 to assess air inversion and local conditions at the rover 12.

The computer system 18 of the rover 12 includes one or more programs 30 that can determine, based on local measurements, when air inversion is appearing or disappearing. The program 30 may employ the temperatures sensed at different heights by the sensors 22 to determine when and if water should be dispensed from sprinkler systems 32 provided on the rover 12 or form sprinklers 34 on or over the ground 28. In other embodiments, the sprinklers system 32 may be located off the rover 12 and may be made responsive to signals generated by the rover 12, e.g., acoustic signals made by the rover 12, or by the computer 16, 18 using rover feedback. The program 30 can consider (as feedback) humidity, dew point, wind velocity, visual conditions (as determined by the imaging device 24), e.g., fog, snow, rain, frost formation, etc.

In one scenario, if the farm is in an area with large topographical changes, cold air may accumulate in a depression more than on a top of a hill, and the cold temperature may stay for a longer period in such a depression. The rover 12 will measure these changes and send the data to the computer system 18 or send the data to the central computer 16. The central computer 16 (or the computer system 18) may control a variable rate irrigation system 34 in the vineyard. The irrigation system 34 in the vineyard irrigates using micro sprinklers 36. When potential for local frost damage occurs, the irrigation system 34 can be turned on to protect the crops. A time response to the treatment can be monitored by the imaging device 24 and the information can be part of a feed-back loop with the cognitive computing platform 40 on the central computer 16 for optimizing the protection or irrigation process. The cognitive computing platform 40 may be stored on one or more of the computing systems 16 and/or 18.

The cognitive computing platform 40 may provide control of the irrigation system 34, portions of the irrigation system 36, control the speed of the rover 12 through the vineyard, control the data rate for sensor data collection, adjust the height at which measurements are acquired, run special checks at particular locations (which may be monitored using the imaging device 24, global positioning data, or other location monitoring system), etc. The cognitive computing platform 40 can evaluate the amount of water delivered to an area using the imaging device 24 or a probe 44 to test the ground saturation at one or more depth. The ground probe measures soil water saturation and can measure soil temperature. The amount of water provided may be based on the sensor measurements, historic data, elevation measurements (e.g., air inversion conditions), etc.

In one embodiment, the system 10 may include a differential irrigation system (34) with comprehensive communication links to receive commands or real time data information from the rover 12 as the rover 12 moves along pre-programed paths in the vineyard or orchard.

The system 10 may perform the following tasks. The rover 12 measures temperature, wind speed, dew point, and relative humidity to determine the needed water to be supplied by the sprinkler system 34. The water may be supplied in different ways/manners (e.g., over the plants, to the ground directly, as snow, as rain, in bursts, steady stream, etc.), at different locations in different amounts in accordance with the measured information by the rover 12. The rover 12 can determine command signals for the sprinkler system(s) 32 and/or 34 to provide the appropriate protection or irrigation, as needed. The settings and commands may be determined by the computing system 18 or central computing system 16. The computing system (16 or 18) can store position based criteria for delivery of water. For example, depending on the time of year, amount of recent rainfall, water table height, position in the vineyard, temperature, humidity, dew point, historic data, etc., an amount of water, a time of delivery (e.g., during the day or night), delivery type, duration, etc. is locally provided.

The rover 12 monitors if enough water is supplied such that everything is saturated, partially saturated, etc. with flowing water. This can be implemented by the imaging device 24 or by a retractable probe 44 on the rover 12 to determine the saturation in the ground 28. The rover 12 can make periodic inspections to determine when it is time to stop the irrigation, and evaluate the results of the treatment via the imaging device 24. The imaging device 24 may view color or other criteria to determine whether sufficient water has been applied to protect from frost or to irrigate the crops. The imaging device 24 may be employed automatically by the computing system (16 or 18) or may be viewed by a user to determine sufficient watering. In one embodiment, the images generated by the imaging device 24 may be employed as a feed-back to the cognitive computing platform 40 to evaluate saturation, frost, etc. The cognitive computing platform 40 can evaluate color, plant state, etc. using recognition software, comparison templates, or other image processing techniques. The rover 12 can receive instructions from the system 16 or 18 to move to a new location and to assess whether frost prevention steps are still needed.

All data from the rover 12 may be saved onboard (in the computing system 18) and/or delivered to the central computing system 16. The differential irrigation system 34 may be actuated by servers (e.g., central computing system 16) to disperse the water using sprinklers 36 of the variable rate irrigation system 34 that can be turned on/off on demand based on the local environment as measured by the rover 12.

In one embodiment, the rover 12 acts as a mobile measurement platform that acquires high resolution environmental parameters as it moves along a predefined path in an orchard or field. Data is transmitted to the system 16 (or system 18) that actuates the variable rate sprinkler system 34 to saturate soil with water a day or two ahead of the expected frost time. This may be based on forecasts of impending cold weather or weather changes sensed locally by the rover 12. The rovers 12 may monitor heat convection from the moist soil during frost time using a heat sensor 46. The rover 12 can provide feedback to the micro sprinkler system or systems 32 or to the sprinkler system 34 to water buds and leaves to maintain flowing water across the ice that encapsulates the buds. Furthermore, the rover 12 can provide images to the cognitive computing platform 40 for an optimization feed-back loop to decide how much water is needed locally.

The sprinkler systems 32 or 34 can dispense water on a canopy of vines based on visual images acquired by the rover 12. The sprinkler systems 32 and/or 34 may include a linear water-pressure response with higher pressure resulting in higher water dispensing rates. The sprinkler systems 32 and/or 34 can be actuated such that they produce snow when directed by the air stratification conditions assessed by the rover 12 and advised by the cognitive computing platform 40 in communication with the rover 12.

Figure 2:
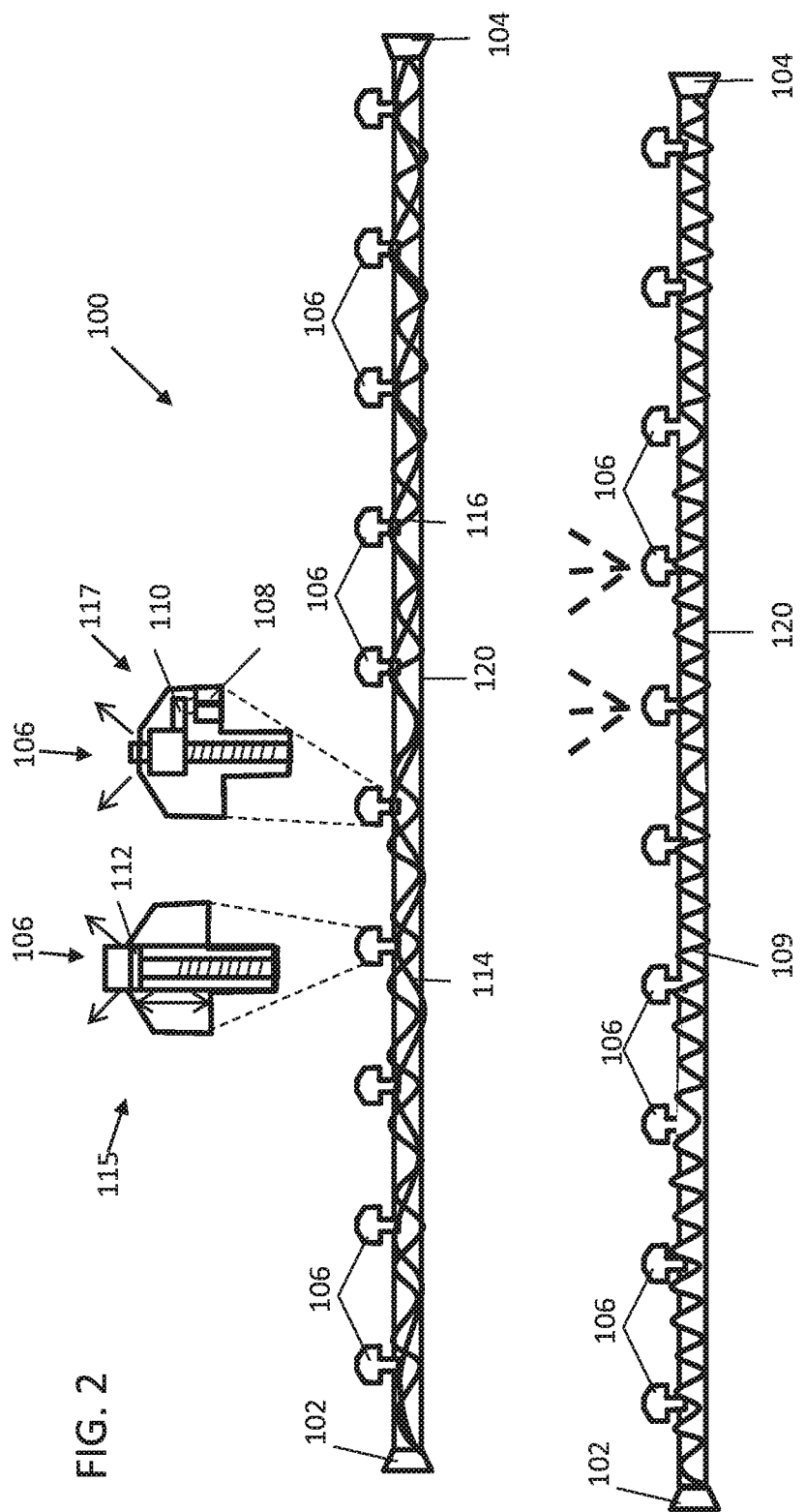
FIG. 2 is a schematic diagram showing a sprinkler system with speakers for an individually activating sprinkler heads acoustically or electrically in accordance with the present principles.

Referring to FIG. 2, a sprinkler system 100 is shown in accordance with one embodiment. The sprinkler system 100 includes a plurality of heads 106 in a pipe or tube 120. In one embodiment, each head 106 includes an actuation frequency that may be the same or different from the other heads in the system 100. The heads 106 are actuated by an acoustic signal or signals. In one embodiment, two speakers 102 and 104 are tuned at different frequencies. In one embodiment, some heads (a first group) 106 are activated when the speaker 102 creates an acoustic wave at a first frequency 114. In another embodiment, some heads 106 (a second group, the same or different heads 106 as the first group) may be activated when the speaker 104 creates an acoustic wave at a second frequency 116. In other embodiments, a standing wave 109 produced when both speakers 102 and 104 are active may set off a third group of sprinkler heads 106, which may include one or more of the other heads in other groups.

In one embodiment, as depicted in exploded view 115, the heads 106 may include a spring-loaded valve 112 that acts as a spring mass system and oscillates in accordance with particular frequencies (resonance frequency). The valve 112 is normally closed, but at the resonance frequency (or other frequency(s), the mass oscillates to release water.

In another embodiment, depicted in exploded view 117, a microphone 108 may receive the frequency for which it is to be activated, and an actuator 110 is activated and opens the spring-loaded valve 112 for that head 106 so that water can be dispensed at a location of interest. When the frequency ceases, the valve 112 is closed by the actuator 110. The rover 12 may generate the frequencies using a horn or speaker 26 (FIG. 1) needed to actuate the heads 106 as well. In this way, localized sprinkler actuation may be achieved. The actuators 110 and microphones 108 in this embodiment may employ a power source, e.g., electrical leads coupled to an AC or DC source (not shown). Other dispensing methods may also be employed to provide area controlled or individually controlled heads 106.

In one embodiment, the shut-off frequency of the heads 106 is different from the turn-on frequency. In this way, data from the rover 12 can be employed to actuate a dispenser which feeds the system 100 and rover measurements close to the sprinkler location can determine the length of irrigation. The rover 12 can provide a turn-off frequency to shut down the heads 106 of the system 100 when enough water has been dispensed. Determining the time when to start the sprinklers and when to shut them off is based on local measurements within the vineyard. For example, the determination of the amount of water is decided based on images, environmental conditions, measurements, etc. from the rover 12, e.g., controlling the rate of water dispensing such that water covers all buds in an image, etc.

In one embodiment, the rover 12 moves along fruit tree lines and measures temperature, relative humidity, etc. while imaging buds and water flow across them. The measurements may be taken at the base level, intermediary level and tree top level of the trees. Different settings for the irrigation system may be employed based on the elevation. For example, water may be needed at the tops of the trees but not at the bottom in frost conditions. The irrigation system can be used for irrigation or used to prevent frost damage. The system 10 (computing system 18 or 16) controls the sprinkle nozzles to minimize frost damage. Each sprinkler/nozzle may have its own resonance frequency (or other control) and at ends of the pipe 120, two speakers 102, 104 can generate an acoustic wave in the pipe 108. Two standing waves 114 and 116 can be created at different frequencies that can be superposed to form a third wave 109 such that each sprinkler/dripper can be excited at its own frequency and at its location by adjusting frequency and/or amplitude of each generated wave. Additional frequencies may also be generated to actuate a larger number of sprinklers of sprinkler groups.

Systems 16 or 18 can receive input from the rover 12 about which spatial area needs to be irrigated more or less, and the central server 16 can actuate irrigation in a well-defined segment of the irrigation line.

Figure 3:
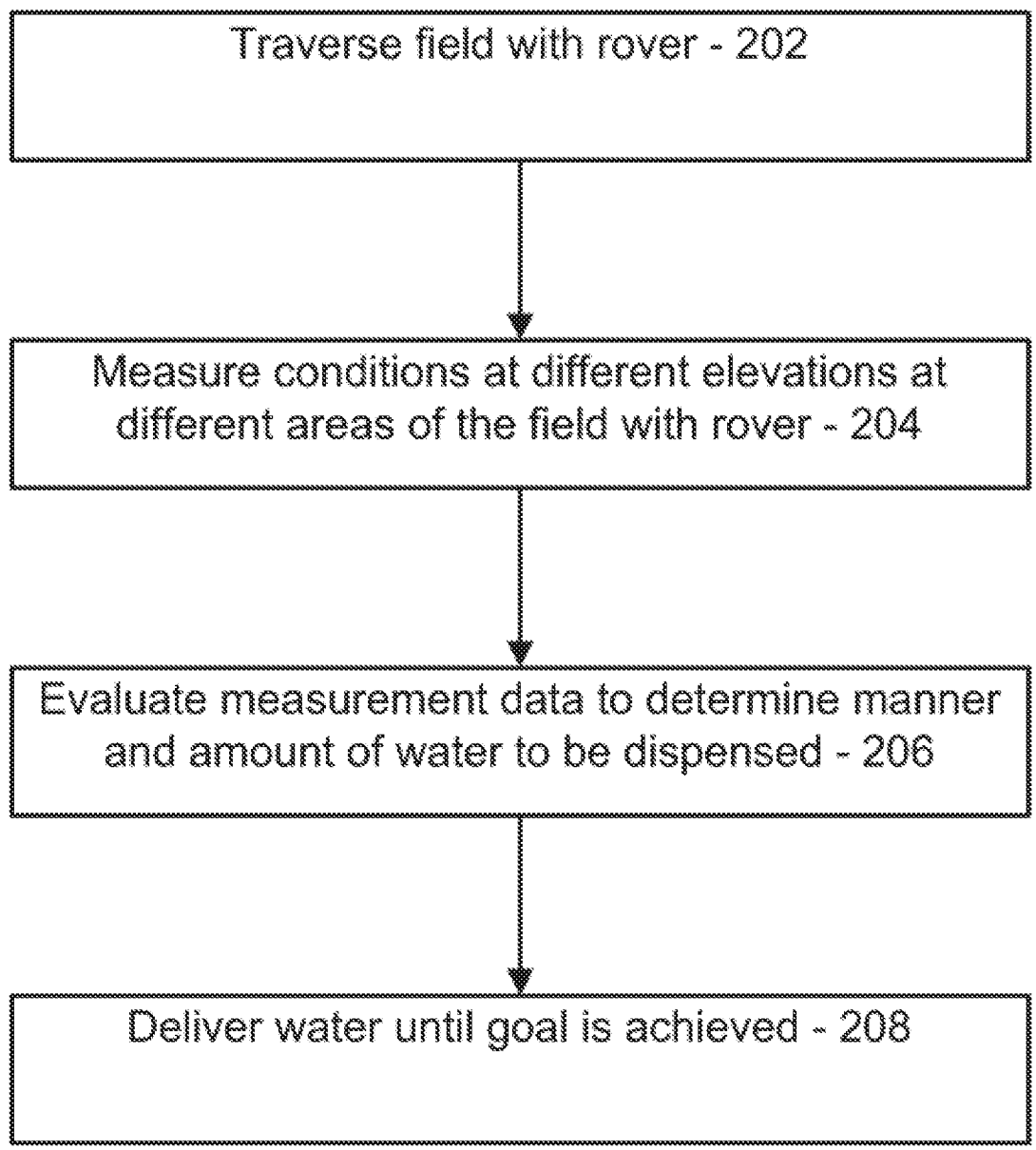
FIG. 3 is a block/flow diagram showing methods for dispensing water for crops in accordance with illustrative embodiments.

Referring to FIG. 3, a method for dispensing water for crops is shown in accordance with illustrative embodiments. In block 202, a field is traversed by a self-propelled rover. The rover includes a tower coupled to a base and extends over the base. A plurality of sensors is set on the tower and the base to sense environmental conditions around the rover at different elevations and at different locations in the field. The rover collects hyper-local information in the field to ensure that the plants/vines are protected from frost and/or properly waters, depending on the season and conditions.

The rover can be relocated to the different locations in the field in accordance with computer control (navigation system, etc.) to map the environmental conditions for the different elevations and at the different locations in the field. The rover may also be equipped with a preprogrammed route that is followed through the field.

In block 204, the environmental conditions are measured using the plurality of sensors on the rover at the different elevations and at the different locations in the field. These measurements can include humidity, temperature, sun angle, dew point, solar radiation strength, wind velocity and direction, etc.

In block 206, local measurement data is evaluated to determine an amount and manner for disbursement of water under the environmental conditions for the different elevations and at the different locations in the field. The amount may be determined based upon current frost conditions, e.g., too much water will weigh down branches, etc., but a sufficient amount is needed to balance trapping energy versus loss due to evaporation. The icing of plant life versus bowing under the weight of ice can be visually evaluated by the cognitive computing platform using visual feedback from the imaging device(s).

In one embodiment, evaluation of the local measurement data includes employing the cognitive computing platform to determine a water delivery rate and a disbursement type to protect plant life from frost damage or irrigate the plant life. For example, a type determined may be made to use overhead sprinklers to generate snow rather than applying liquid water to the plants or misting versing sprinkling, etc. Another manner/type may include the rate and amount at which the water in delivered. This may be determined by the cognitive computing platform based on many present conditions/other data as well and past or forecasted conditions. Other data may include one or more of historic weather data, seasonal data, forecasted weather, etc. The water may be dispensed in one single time block if the temperature is close to the freezing point or it can be a dispensed in small bursts to assure no freezing occurs.

In block 208, the water is delivered until goal conditions are met. Goal conditions may include an amount of saturation, an ice coating that doesn't stress the branches of plants, etc. The water delivery may include activating a sprinkler system locally and monitoring the water on the plant life using at least one of an imaging system and/or a ground probe. The delivering of the water may include using individually controlled sprinkler sections or individually controlled heads. In one embodiment, the heads are acoustically activated sprinkler heads disposed locally throughout the field.

This process may be iterated to maintain conditions in a field or to further monitor the conditions for changes. The rover may also be employed for other purposes. For example, scaring off animals that might damage the crops, etc.

Having described preferred embodiments autonomous mobile platform and variable rate irrigation method for preventing frost damage (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims.

Having thus described aspects of the invention, with the details and particularity required by the patent laws, what is claimed and desired protected by Letters Patent is set forth in the appended claims:

1. A rover, comprising:
a base having wheels;
a propulsion system coupled to the wheels to propel the rover around a field;
a tower coupled to the base and extending over the base;
a plurality of sensors set on the tower and the base and configured to sense environmental conditions around the rover at different elevations; and
a computing system including a processor and memory, the memory including computer program code that causes the processor to receive measured data from the plurality of sensors, to predict a future weather condition, to determine an amount and manner of water to be dispensed on plant life in the field to protect the plant life from the future weather condition, and to control a separate, stationary sprinkler system that includes a plurality of individually controllable heads that are controlled to deliver the water to be dispensed in accordance with the measured data and predicted local conditions.

2. The rover as recited in claim 1, wherein the plurality of sensors measure one or more of temperature, humidity and wind velocity at the different elevations.

3. The rover as recited in claim 1, wherein the rover includes a sprinkler system onboard to deliver the water to be dispensed.

4. The rover as recited in claim 1, wherein the rover communicates with a central computer system which controls a separate sprinkler system to deliver the water to be dispensed in accordance with the measured data.

5. The rover as recited in claim 1, further comprising an imaging device mounted on the rover to evaluate water delivery amounts for the plant life in the field using visual feedback.

6. The rover as recited in claim 1, wherein the propulsion system moves the rover through the field to evaluate a plurality of different locations in the field in accordance with the environmental conditions.

7. The rover as recited in claim 1, wherein the computing system is further configured to identify an air inversion condition from the received measured data.

8. The rover as recited in claim 7, wherein the computing system is further configured to determine the amount of water to be dispensed based on the identified air inversion condition.

9. The rover as recited in claim 1, wherein the rover uses acoustic signals to control the stationary sprinkler system, with a separate frequency being used to control each respective head of the plurality of individually controllable heads.

* * * * *